United States Patent
Zhang et al.

(10) Patent No.: US 11,398,064 B2
(45) Date of Patent: Jul. 26, 2022

(54) REAL TIME RECONSTRUCTION-NATIVE IMAGE ELEMENT RESAMPLING FOR HIGH DEFINITION IMAGE GENERATION AND PROCESSING

(71) Applicant: KONINKLIJKE PHILIPS N.V., Eindhoven (NL)

(72) Inventors: Bin Zhang, Cleveland, OH (US); Chuanyong Bai, Solon, OH (US); Andriy Andreyev, Willoughby Hills, OH (US); Zhiqiang Hu, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 91 days.

(21) Appl. No.: 16/648,760

(22) PCT Filed: Sep. 18, 2018

(86) PCT No.: PCT/EP2018/075153
§ 371 (c)(1),
(2) Date: Mar. 19, 2020

(87) PCT Pub. No.: WO2019/057689
PCT Pub. Date: Mar. 28, 2019

(65) Prior Publication Data
US 2020/0250862 A1 Aug. 6, 2020

Related U.S. Application Data

(60) Provisional application No. 62/560,720, filed on Sep. 20, 2017.

(51) Int. Cl.
*G06T 11/00* (2006.01)
*G16H 30/20* (2018.01)

(52) U.S. Cl.
CPC .......... *G06T 11/008* (2013.01); *G16H 30/20* (2018.01); *G06T 2211/428* (2013.01)

(58) Field of Classification Search
CPC .. G06T 11/008; G06T 2211/428; G16H 30/20
See application file for complete search history.

(56) References Cited

U.S. PATENT DOCUMENTS 7,317,456 B1 * 1/2008 Lee ................. G06T 15/08
345/427
2009/0123042 A1 5/2009 Gagnon

FOREIGN PATENT DOCUMENTS

WO 2006054193 A1 5/2006
WO 2012077109 A2 6/2012

OTHER PUBLICATIONS

International Search Report and Written Opinion of PCT/EP2018/075153, dated Jan. 11, 2019.
(Continued)

*Primary Examiner* — Manuchehr Rahmjoo (57) ABSTRACT

A non-transitory computer-readable medium stores instructions readable and executable by a workstation (14) operatively connected to a display device (20) and including at least one electronic processor (16) to perform an image acquisition and reconstruction method (101). The method includes: retrieving a non-voxel-based reconstructed image comprising non-voxel image elements from a picture and archiving communication system (PACS) database (24) to the workstation; at the workstation, generating at least one voxel-based resampled image from the non-voxel-based reconstructed image; and displaying the at least one voxel-based reconstructed image on the display device.

17 Claims, 4 Drawing Sheets

(56) References Cited

OTHER PUBLICATIONS

Liao, Duoduo "GUP-Accelerated Multi-Valued Solid Voxelization by Slice Functions in Real Time", Computer Graphics, ACM, Apr. 2008, pp. 113-120.
Niebner, Matthias et al "Real-Time 3D Reconstruction at Scale using Voxel Hashing", ACM Transactions on Graphics, Nov. 2013, pp. 1-11.

* cited by examiner

REAL TIME RECONSTRUCTION-NATIVE IMAGE ELEMENT RESAMPLING FOR HIGH DEFINITION IMAGE GENERATION AND PROCESSING

CROSS-REFERENCE TO PRIOR APPLICATIONS

This application is the U.S. National Phase application under 35 U.S.C. § 371 of International Application No. PCT/EP2018/075153, filed on Sep. 18, 2018, which claims the benefit of U.S. Provisional Patent Application No. 62/560,720, filed on Sep. 20, 2017. These applications are hereby incorporated by reference herein.

FIELD

The following relates generally to the medical imaging arts, medical image interpretation arts, image reconstruction arts, and related arts.

BACKGROUND

Lower dose and higher image resolution are two clear trends in medical imaging of transmission computed tomography (CT), positron emission tomography (PET), and single photon emission computed tomography (SPECT). However, these trends can lead to sparsity of counts for many voxels of the image. A lower dose means that there are fewer counts overall, and hence fewer counts on average for each voxel. Higher resolution means smaller voxels, again leading to fewer counts on average per voxel.

Reconstruction native elements, such as blob basis function and nature voxels, have been used and studied in PET imaging as an alternative to voxels in image reconstruction for its unique properties in balancing the trade-off between noise control and resolution recovery. In practice, these non-voxel reconstruction-native elements are usually defined on their own special grid that may or may not relate to the Cartesian grid of voxels. For example, spherical blob basis functions are commonly defined based on the body-centered cubic (BCC) grid. Neighboring blob elements overlap, which helps counter the count sparsity issue by, in effect, "sharing" counts (with different weightings) amongst two or more blob elements. Another illustrative non-voxel image element is a point cloud.

However, images represented by these non-voxel reconstruction-native elements are hard to be directly displayed or digitally processed. Moreover, clinicians are used to the concept of images represented by voxels, where image intensity is definitively grouped into discrete non-overlapping voxels, which are commonly aligned with conventional coronal, sagittal, and axial anatomical directions, and concepts such as voxel resolution are readily comprehensible. For example, a physician readily understands that an image with smaller voxel size provides higher resolution than an image with larger voxel size; but may not so readily comprehend the import of a blob element having a statistical or probabilistic interpretation which varies with distance from the geometric center of the blob and overlaps with neighboring blobs.

A common way of solving this problem is to perform the reconstruction using non-voxel native reconstruction elements, such as blobs, and then after the reconstruction is complete to perform a reconstruction-element-to-voxel conversion on the final reconstructed image with reconstruction-native elements to generate a voxel image with a predefined voxel size. The converted voxel image is then stored in a Picture Archiving and Communication System (PACS) database and retrieved and used by the image viewer or post-reconstruction image processors to perform image display and optional further image processing based on the user's need. The reconstructed image in non-voxel elements is usually discarded and not used in post-reconstruction image processing. This approach effectively combines the benefits of non-voxel native reconstruction elements for combating counts sparsity due to low dose and/or high resolution image reconstruction with the benefits of providing the clinician with images in the desired, and familiar, voxel-based format. However, because the reconstructed image in non-voxel elements is discarded, if later on one needs to obtain a voxel-based image in different orientation or with different voxel size, one has to either (a) re-reconstruct the non-voxel based image and resample it to the desired voxel-based image or (b) use the saved voxel-based image to downsample or up-sample to the desired voxel size or rotate to the desired orientation, or the combination of (a) and (b). The first option can lead to concerns on efficiency and work/data flow for clinical applications. However, the second option can lead to concerns on image quality, especially over smoothing and loss of resolution due to interpolations in rotation and information loss during the initial resampling from the non-voxel image to the save voxel-based image and the later on interpolation from the saved voxel-based image to the desired voxel-based image with different voxel size.

The following discloses new and improved systems and methods to overcome these problems.

SUMMARY

In one disclosed aspect, a non-transitory computer-readable medium stores instructions readable and executable by a workstation operatively connected to a display device and including at least one electronic processor to perform an image acquisition and reconstruction method. The method includes: retrieving a non-voxel-based reconstructed image comprising non-voxel image elements from a picture and archiving communication system (PACS) database to the workstation; at the workstation, generating at least one voxel-based resampled image from the non-voxel-based reconstructed image; and displaying the at least one voxel-based resampled image on the display device.

In another disclosed aspect, an imaging system includes an image acquisition device configured to acquire imaging data of a patient. A reconstruction device is programmed to generate a non-voxel-based reconstructed image from the imaging data using non-voxel image elements selected from at least one of blob elements, point cloud elements, or spatially overlapping image elements. The system also includes a display device. At least one electronic processor is programmed to: retrieve the non-voxel-based reconstructed image comprising non-voxel image elements from a picture and archiving communication system (PACS) database to a workstation; at the workstation, generate at least one voxel-based resampled image from the non-voxel-based reconstructed image; and control the display device to display the at least one voxel-based resampled image on the display device.

In another disclosed aspect, an imaging system includes an image acquisition device configured to acquire imaging data of a patient. A reconstruction device is programmed to generate a non-voxel-based reconstructed image from the imaging data using non-voxel image elements selected from at least one of blob elements, point cloud elements, or_ spatially overlapping image elements. A picture and archiving communication system (PACS) database is configured to store the non-voxel-based reconstructed image. A workstation includes a display device, a user input device, and at least one electronic processor programmed to: retrieve the non-voxel-based reconstructed image comprising non-voxel image elements from the PACS database to a workstation; at the workstation, generate at least one voxel-based resampled image from the non-voxel-based reconstructed image, the different voxel-based resampled images differing by at least one of different voxel sizes and different voxel coordinate orientations; and control the display device to display the at least one voxel-based resampled image on the display device.

One advantage resides in using non-voxel based elements to avoid voxel based image interpolation in image resampling.

Another advantage resides in using a real time non-native image element to perform a voxel conversion to allow for pixel size independent non-native element reconstruction, or non-native element parameters optimized for the range of pixel sizes desired for the voxel-based images. There would be no need to vary the non-native element parameters for the reconstruction using non-native elements.

Another advantage resides in overlapping non-native elements to reduce number of elements needed to represent a reconstructed image.

Another advantage resides in more efficient reconstruction elements with smaller size files for storage and transfer.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

In existing clinical imaging, image reconstruction is performed at a reconstruction server, and the output is a voxel-based image that is stored in a Picture Archiving and Communication System (PACS) database. The reconstruction may employ image elements (referred to herein as "reconstruction-native image elements") that differ from the voxels of the stored voxel-based image. For example, the reconstruction may employ higher resolution voxels. In addition, non-voxel image elements may be used, such as blobs or point clouds or meshes. Again, the image is converted to the clinical-standard-size voxels for storage in the PACS.

Thereafter, the clinician operates a workstation viewer to download the voxel-based reconstructed image. If the image is zoomed, the voxels are up-resampled to provide the requested higher resolution. In cardiac studies, another common operation is to extract image slices along directions oblique to the imaging coordinates (e.g. axial, sagittal, and coronal) so as to align with anatomical axes of the heart.

As recognized herein, issues with this practice can arise. The user often wants to perform post-reconstruction image processing. Using the existing approach, post-reconstruction image processing methods, such as ROI zooming, image resampling for image fusion, image re-slicing or re-orientating for special clinical application, image comparison, and image enhancement, have to rely on voxel grid interpolation operating on the converted voxel-based image. Voxel grid interpolation can introduce image blurring and lose of feature quantification. More fundamentally, when the reconstructed image represented in non-voxel reconstruction-native image elements, such as blobs or point clouds, is converted to a voxel-based image for storage in the PACS, this results in a loss or degradation of image information content, and any post-reconstruction processing performed on the voxel-based image may further reduce or degrade the image information content.

For example, up-sampling cannot actually recover resolution beyond that captured at the voxel size of the stored voxel-based image. Likewise, extraction of an oblique image slice can introduce interpolation errors.

The following discloses approaches entailing storing the "raw" reconstructed image represented using the reconstruction-native image elements in the PACS, and adding processing power to the workstation viewer to convert the image in this format to the voxel-based image requested by the clinician.

In some embodiments, an imaging technician performing the image reconstruction can choose the reconstruction-native image elements to support the anticipated post-reconstruction processing (e.g. zoom, oblique slice extraction, and the like). For zoom, this means the reconstruction-native image elements should have the maximum resolution that may credibly be desired by a clinician. For oblique slice extraction, the reconstruction-native image elements are preferably isotropic or at least have smaller-angle rotational symmetry, e.g. a body-centered cubic (BCC) blob has primitive planes along angles 45° to the axial, sagittal, and coronal planes, while a point cloud may have spherical symmetry.

The reconstruction-native elements described herein may comprise spherical blob basis functions but not limited to it. A non-limiting illustrative example of a spherical blob basis function (i.e. blob reconstruction element) employing a Kaiser-Bessel function is (see, e.g. Gagnon et al., U.S. Pub. No. 2009/0123042 A2):

$$b_{m,a,\alpha}(r) = \begin{cases} \frac{1}{I_m(\alpha)}\left(\sqrt{1-\left(\frac{r}{a}\right)^2}\right)^m I_m\left(\alpha\sqrt{1-\left(\frac{r}{a}\right)^2}\right), & \text{for } 0 \leq r \leq a \\ 0, & \text{otherwise} \end{cases} \quad (1)$$

where $I_m$ is a Bessel function of order m, a is the blob radius, and $\alpha$ is a tapering parameter. In some approaches, the blobs are positioned at lattice points of a face-centered cubic (FCC) lattice, and if the blob radius is larger than the spacing between lattice points then neighboring blob elements will spatially overlap. This is merely an illustrative example, and other elements such as blob elements with different decay functions besides the illustrative Bessel function, or point clouds or nature pixel/voxels, may also be used. To represent an image using such elements, a weighted sum is used (see, e.g. Gagnon et al., U.S. Pub. No. 2009/0123042 A2):

$$f(x, y, z) = \sum_{all\ l=(x_l,y_l,z_l)\in L} c_l b_{m,a,\alpha}(x - x_l, y - y_l, z - z_l) \quad (2)$$

where L denotes the lattice (e.g. a BCC lattice spanning the volume of the reconstructed image in one embodiment), l is a point of the lattice L having spatial coordinates $(x_l, y_1, z_1)$, $c_1$ is the weight assigned to the blob at the lattice point l, and the summation is over all lattice points of the lattice L. Typically, the blob parameters (radius a and tapering α) are the same for all blobs (that is, the same for all l∈L), although it is contemplated to use different blob parameters for certain spatial regions, e.g. smaller radius and/or sharper tapering to provide higher resolution in critical regions. The optimization of the weights $c_1$ may be done, for example, using an iterative optimization such as Maximum Likelihood-Expectation Maximization (ML-EM), Ordered Subsets Expectation Maximization (OSEM), or other iterative image reconstruction approach. The reconstructed blob image can be used as a "base" image for post-reconstruction image display and image processing instead of the cubic voxel image converted from the image represented by reconstruction-native elements at the end of the image reconstruction. The blob-to-voxel conversion is performed in real-time per the need of the image processing job. Because of the overlapping, spherically-symmetric nature of the blob basis function, the blob image keeps a semi-continuous representation of the activity distribution which is more realistic and better preserves image feature details for image reprocessing than cubic voxel based up-sampling.

In some embodiments, voxel based image interpolation can be avoided for any image resampling, such as changing the image with large/small voxel size to an image with small/large voxel size, and zooming on a chosen ROI. Similarly, when frequent image slices are extracted, which is common in CT operations, and reorientation (such as in cardiac applications) are needed, a newly re-sliced or reoriented image can be created directly from blob image, rather than to go through an intermediate voxel image conversion step.

In other embodiments, a real time need-based blob-voxel conversion allows pixel size independent blob reconstruction. The blob basis functions can be chosen based on the statistics of the data and the geometrical response of the scanning system, and not dependent on the required output image voxel size. In this way, the blob can be designed to optimize the best feature preservation and noise control outcome without being limited on the use of certain output voxel grid.

In further embodiments, the extended spatial support, overlapping nature and efficient arrangement into body-centered cubic grids of blobs can significantly reduce the total number of elements used to represent an image, which means blob image is more efficient in I/O handing and requires less disk space to save.

The following illustrative systems and methods can implement any iterative reconstruction algorithm that reconstructs a three-dimensional (3D) image using blob basis functions. A digital image display/processing system that can perform on-the-fly real time blob-to-voxel conversion of an input blob image, and then apply digital processing (e.g. zooming, filtering, reorientation, and the like) of the resultant image.

Figure 1:
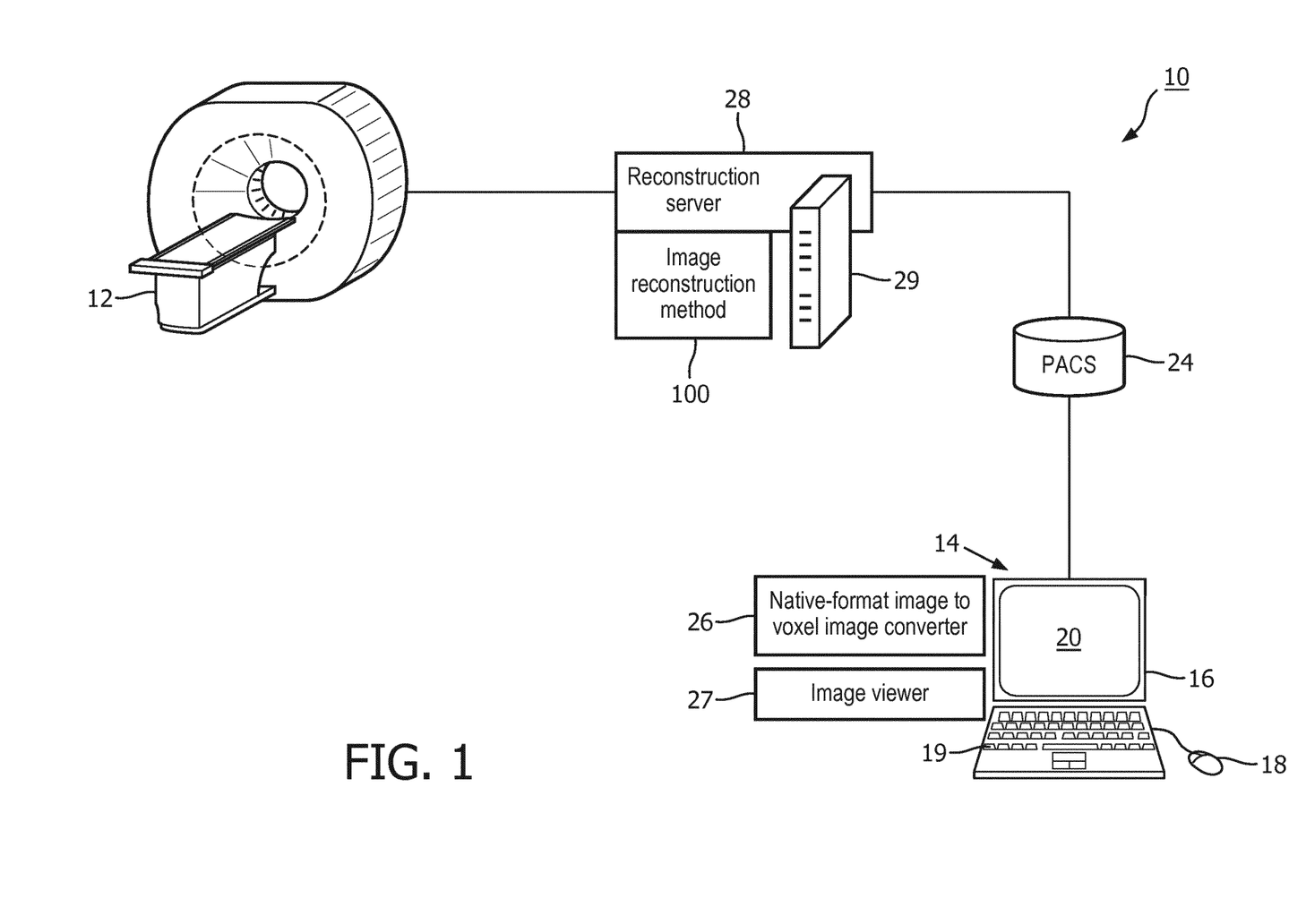
FIG. 1 diagrammatically shows image reconstruction system according to one aspect.

With reference to FIG. 1, an illustrative medical imaging system 10 is shown. As shown in FIG. 1, the system 10 includes an image acquisition device 12. In one example, the image acquisition device 12 can comprise an emission imaging device (e.g., a positron emission tomography (PET) device, a single photon emission computed tomography (SPECT) device, and the like); however, it will be appreciated that any other suitable imaging modality (e.g., magnetic resonance, transmission computed tomography (CT), ultrasound, X-ray, and the like, as well as hybrid systems, such as PET/CT) may be used.

The system 10 also includes a computer or workstation or other electronic data processing device 14 with typical components, such as at least one electronic processor 16, at least one user input device (e.g., a mouse 18, a keyboard 19, a trackball, and/or the like), and a display device 20. In some embodiments, the display device 20 can be a separate component from the computer 14. The workstation 14 can also include or have operative access to one or more databases (stored in a non-transitory storage medium such as ROM, a magnetic disk, RAID disk array, or so forth) (e.g., an electronic medical record (EMR) database, an illustrative picture archiving and communication system (PACS) database 24, and the like). As used herein, the database 24 refers to a PACS database. As used herein, the term "PACS" and similar nomenclature refers generally to any clinical imaging database, e.g. a named PACS database, or a Radiology Information System (RIS), or domain-specific database such as a Cardiovascular Information System (CVIS), or so forth. The workstation 14 also is configured to read and execute instructions stored on a non-transitory storage medium (e.g. hard disk drive, solid state drive, et cetera) to implement an element-to-voxel converter 26 to convert an image represented in non-native image elements (i.e., non-voxel based) of a reconstructed image into an image represented by voxel elements; and to implement an image viewer 27 providing a clinician with the ability to view and manipulate voxel-based images. The system 10 also includes a reconstruction device 28 (e.g., a server computer, cloud computing resource, or other electronic processor 29 typically associated with the image acquisition device 12) different from the workstation 14. The reconstruction device 28 is configured to receive imaging data from the image acquisition device 12, perform an image reconstruction process, and save the reconstructed images into the PACS 24.

The electronic processor 29 is operatively connected with a non-transitory storage medium (not shown) that stores instructions which are readable and executable by the electronic processor 29 to perform disclosed operations including performing an image acquisition reconstruction method or process 100. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the image reconstruction method or process 100 may be performed by cloud processing.

The electronic processor 16 of the workstation 14 is operatively connected with a non-transitory storage medium (not shown) that stores instructions which are readable and executable by the electronic processor 16 to perform disclosed operations including performing the image converter method or process 26 and implementing the image viewer 27. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

Figure 2:
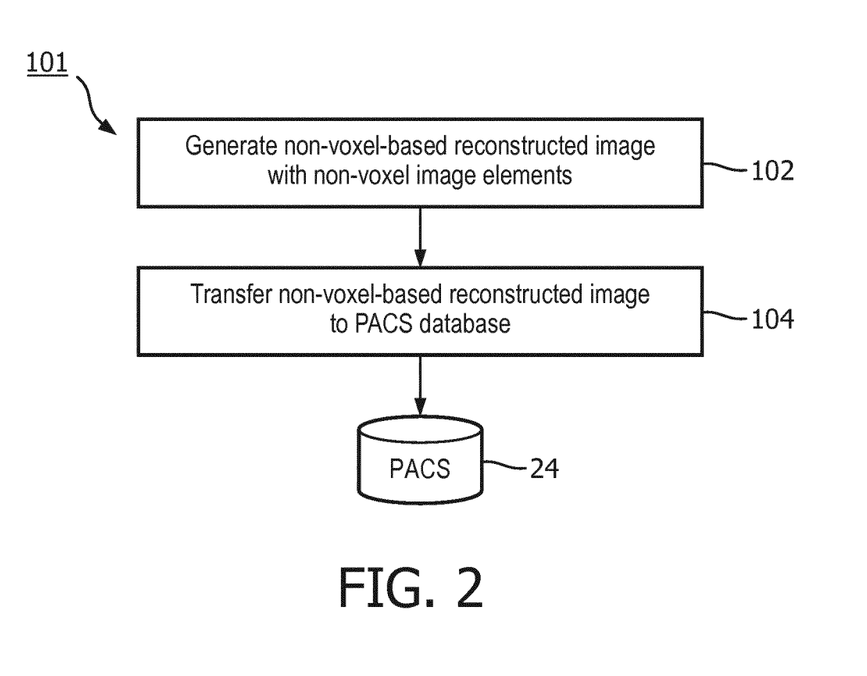
FIGS. 2 and 3 show exemplary flow chart operations of components of the system of FIG. 1.

With reference to FIG. 2, an image acquisition and reconstruction method 101 is diagrammatically shown as a flowchart. At 102, a non-voxel-based reconstructed image is generated. To do so, the image acquisition device 12 acquires imaging data of patient. The imaging data is sent to the reconstruction device 28, which performs the image reconstruction process 100 that optimizes non-voxel image elements in the imaging data to generate the non-voxel-based reconstruction (i.e., a native-format) image. In some embodiments, the non-voxel image elements are selected from blob elements, point cloud elements, or spatially overlapping image elements. The spatially overlapping elements are configured such that at least neighboring non-voxel image elements spatially overlap in the non-voxel-based reconstructed image. In one approach, the image is generated as the weighted sum of Equation (2) of the blob elements of Equation (1), with each blob element assigned a weight, and the image reconstruction iteratively optimizes the weights of the blob elements, e.g. using a Maximum Likelihood-Expectation Maximization (ML-EM), Ordered Subsets Expectation Maximization (OSEM), or other iterative image reconstruction approach.

In some embodiments, the reconstruction device 28 is further configured to optimize the non-voxel image elements for a maximum voxel resolution value of the selected non-voxel image element. For example, the blob radius and tapering parameters of the blob basis function of Equation (1) control the spatial extent of the blob. A tighter blob (smaller radius and/or sharper tapering) provides improved spatial resolution, though possibly at the cost of more sparsity since the tighter blobs may (on average) have less contribution from imaging data counts. For certain types of clinical imaging higher resolution may be desired as compared with other types of clinical imaging. In one approach, a table of blob parameters for different imaging types are stored (e.g. for different anatomical regions imaged, and/or imaging study orders from different clinical departments such as cardiology versus oncology), and the blob parameters for the specific imaging study type are retrieved and used in the image reconstruction process 100.

At 104, the non-voxel-based reconstructed image is transferred from the reconstruction device 28 to the PACS database 24. The non-voxel-based reconstructed image is stored in the PACS database 24 in its native non-voxel format. Using the continuing example of an image reconstructed using the blob elements of Equation (1), this entails storing the set of blobs with weights optimized by the image reconstruction. In one suitable approach, this entails storing the blob radius and tapering parameters (which are typically not necessarily the same for all blob elements of the image), and storing the optimized weight for each blob. In some cases, storage of the image in this information-rich non-voxel reconstruction-native elements format may be more compact than storing the image converted to voxels (as in the conventional approach).

Figure 3:
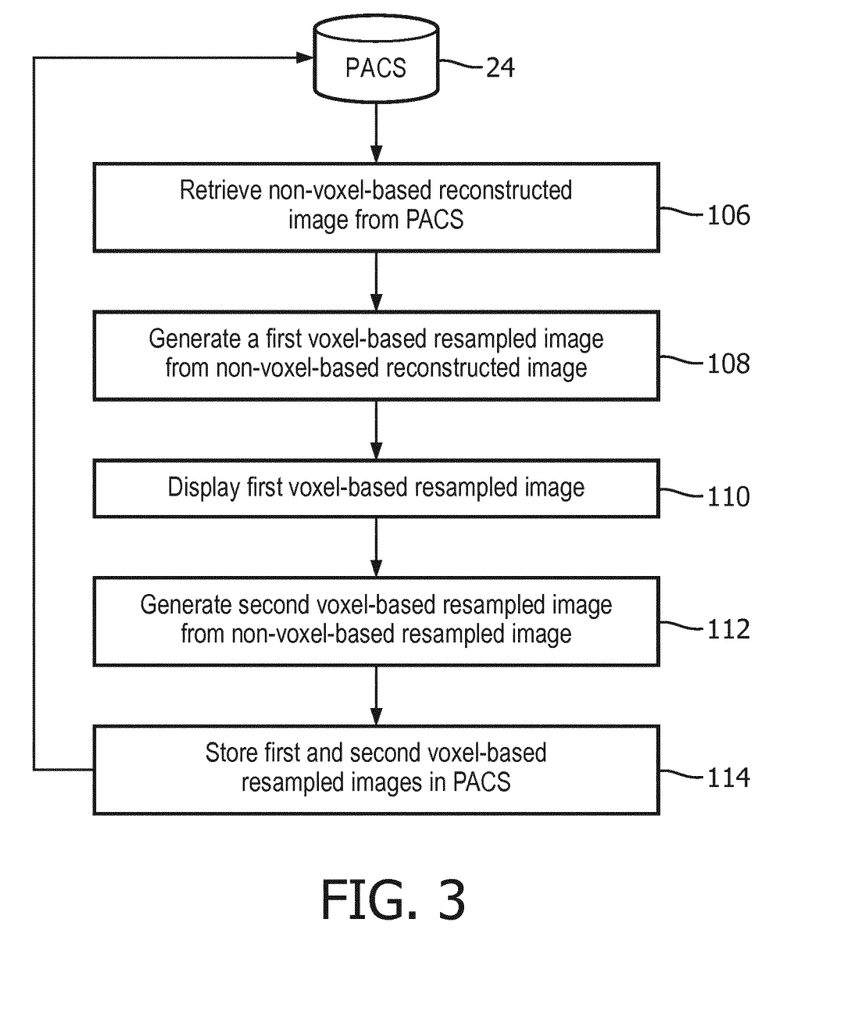

With reference to FIG. 3, image viewing and manipulation operations performed at the workstation 14 (that is, by the electronic processor 16) are described.

At 106, the at least one electronic processor 16 is programmed to retrieve the non-voxel-based reconstructed image from the PACS database 24 to the workstation 14.

At 108, the at least one electronic processor 16 is programmed to generate a first voxel-based resampled image from the non-voxel-based reconstructed image at the workstation 14. This is the function of the image converter 26 of FIG. 1. To do so, the element-to-voxel converter 26 is programmed to convert the blob elements of the non-voxel-based reconstructed image to voxels to generate the first voxel-based resampled image. In one approach for doing so, Equation (2) is applied with the resampled-optimized weights for the blobs. In one specific approach, Equation (2) is evaluated at the (x,y,z) coordinates of the voxel center to obtain the value for that voxel. A more precise value may be obtained, especially in the case of coarser voxels, by evaluating Equation (2) at several such coordinates within the voxel and taking an average. In evaluating the sum of Equation (2), it may be noted that blobs whose location is further away from the evaluation point (x,y,z) than the blob radius a may be omitted since by Equation (1) their contribution to the evaluation point (x,y,z) is identically zero. In some examples, one or more region of interest parameters (e.g., a maximum or minimum standard uptake value (SUVmax, SUVmin), a standard uptake value mean (SUVmean), a standard uptake value standard deviation (SUVstdev) and the like) of the non-voxel image elements of the non-voxel-based reconstructed image are determined to determine the corresponding voxels of the first voxel-based resampled image.

At 110, the at least one electronic processor 16 is programmed to control the display device 20 of the workstation 14 to display the first voxel-based resampled image. This is suitably performed by the image viewer 27 of FIG. 1. Typically, the image viewer 27 does not merely display the image, but also allows for the user to perform various manipulations on the image. In some embodiments, the image viewer 27 provides a radiology reading environment including provision of windows and user interfacing for entry of a radiology report (e.g. using the keyboard 19 and/or a dictation microphone) and for performing image processing operations such as measuring dimensions of a lesion or other image feature using cursors moved via the mouse 18, or so forth.

At 112, the at least one electronic processor 16 is programmed to generate a second voxel-based resampled image defined by user operations performed on the first voxel-based resampled image. These operations are suitably implemented by the image viewer 27, and may for example entail zooming in on a particular region of the image (thus requiring re-sizing to higher-resolution voxels), selecting an oblique slice through the heart or other organ (thus requiring defining voxels for a different coordinates orientation), or so forth. The different first and second voxel-based resampled images differ by at least one of different voxel sizes and different voxel coordinate orientations. In some embodiments, where the non-voxel image elements are optimized for the maximum voxel resolution value, the plurality of resampled images includes a voxel-based resampled image generated with the maximum voxel resolution and a voxel-based resampled image generated with the voxel resolution that is coarser than the maximum resolution. The at least one electronic processor 16 is programmed to generate the at least one voxel-based resampled image from the at least one non-voxel-based reconstructed image in real time.

To generate the second voxel-based image, the at least one electronic processor 16 is programmed to receive one or more user inputs via the user input device 18 of the workstation 14. The user inputs are indicative of a selection by the clinician of a region of the first-voxel based resampled image that is displayed on the display device 20. The electronic processor 16 is programmed to generate the second voxel-based resampled image as a resampling of the selected region of the first voxel-based reconstructed image reconstructed using a different voxel size than that of the first voxel-based reconstructed image. To do so, the element-tovoxel converter 26 is programmed to convert the blob elements of the non-voxel-based reconstructed image to voxels to generate the second voxel-based resampled image. The selection of the region and the generation of the second voxel-based reconstructed image implements a zoom operation indicative of the user inputs received via the user input device 18.

In another example, to generate the second voxel-based image, the at least one electronic processor 16 is programmed to receive one or more user inputs via the user input device 18 of the workstation 14. The user inputs are indicative of a selection by the clinician of a voxel coordinate orientation in the displayed first voxel-based reconstructed image. The selected voxel coordinate orientation is different from a voxel coordinate orientation of the first voxel-based resampled image. In some examples, the electronic processor 16 is programmed to generate the second voxel-based resampled image in which the second voxel-based resampled image has the selected voxel coordinate orientation. To do so, the element-to-voxel converter 26 is programmed to convert the blob elements of the non-voxel-based reconstructed image retrieved at 106 from the PACS 24 to voxels to generate the second voxel-based resampled image. In other words, the second voxel-based resampled image is not generated by resampling the first voxel-based resampled image; rather, the second voxel-based resampled image is independently generated from the same non-voxel-based reconstructed image that was previously converted to generate the first voxel-based reconstructed image. This is feasible because the conversion is performed by the image converter 26 running on the same workstation 14 that implements the image viewer 27, rather than being done at the reconstruction server 28. This is made feasible also because the non-voxel-based reconstructed image is stored at the PACS 24, rather than the stored converted voxel-based image. In one illustrative example, the first voxel-based reconstructed image may be a heart of the patient reconstructed along the axial, sagittal, coronal anatomical directions. The second voxel-based resampled image may be reconstructed along major and minor axes of the heart which are oblique to the axial, sagittal, and coronal planes. In other examples, the selection of the voxel coordinate orientation and the generation of the second voxel-based reconstructed image implements a slice extraction operation. The second voxel-based reconstructed image is an image slice aligned with the selected voxel coordinate orientation.

At an optional operation 114, the first and second voxel-based resampled images are stored in the PACS database 28. Alternatively, only the non-voxel-based reconstructed image remains stored at the PACS 28, and the voxel based images are created (or re-created) on demand using the image converter 26.

Figure 4:
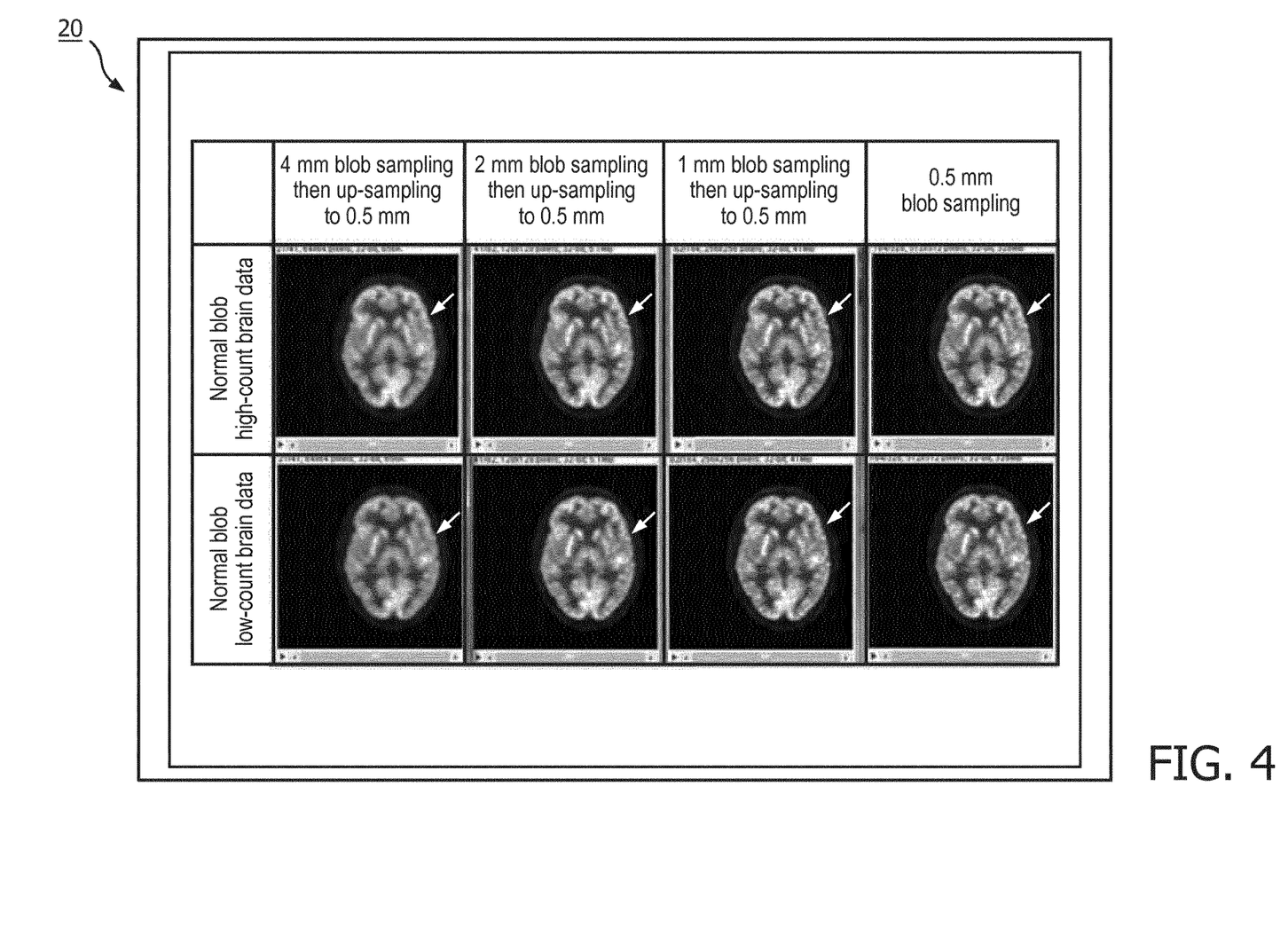
FIG. 4 illustratively shows a display of the system of FIG. 1.

FIG. 4 shows a comparison study that evaluates the benefit of blob resampling versus voxel resampling. It can be seen that using direct blob resampling to generate a high definition image preserves feature better than using voxel-based up-sampling to up-sample a low-definition image to a high-definition image. As shown in FIG. 4, as the size of the blob sampling parameter decreases, the resolution of the reconstructed image increases.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory computer-readable medium storing instructions readable and executable by a workstation operatively connected to a display device and comprising at least one electronic processor to perform an image acquisition and reconstruction method, the method comprising:
   retrieving a non-voxel-based reconstructed image of an imaging modality comprising non voxel image elements from a picture and archiving communication system (PACS) database to the workstation;
   at the workstation: generating at least one voxel-based resampled image of the imaging modality from the non-voxel-based reconstructed image wherein the at least one voxel-based resampled image comprises at least two different voxel-based resampled images; generating, in real-time, the at least two different voxel-based resampled images from the non-voxel-based reconstructed image, wherein the different voxel-based resampled images differ by at least one of different voxel sizes and different voxel coordinate orientations;
   displaying the at least one voxel-based resampled image on the display device; and
   displaying, on the display device, a first voxel-based resampled image of the at least two different voxel-based resampled images;
   receiving one or more user inputs, via a user input device of the workstation, indicative of a selection of a region of the first voxel-based resampled image; and
   generating a second voxel-based resampled image of the at least two different voxel-based resampled images from the non-voxel-based reconstructed image, wherein the second voxel-based resampled image is a resampling of the selected region of a first voxel-based reconstructed image resampled using a different voxel size than that of the first voxel-based resampled image from the non-voxel-based reconstructed image.

2. The non-transitory computer-readable medium of claim 1, wherein the selection of the region and the generation of the second voxel-based reconstructed image implements a zoom operation.

3. The non-transitory computer-readable medium of claim 1, wherein the method further comprises:
   displaying, on the display device, a first voxel-based reconstructed image of the at least two different voxel-based reconstructed images;
   receiving one or more user inputs, via a user input device of the workstation, indicative of a selection of a voxel coordinate orientation in the displayed first voxel-based resampled image wherein the selected voxel coordinate orientation is different from a voxel coordinate orientation of the first voxel-based resampled image; and
   generating a second voxel-based resampled image of the at least two different voxel-based resampled images from the non-voxel-based reconstructed image wherein the second voxel-based reconstructed image has the selected voxel coordinate orientation.

4. The non-transitory computer-readable medium of claim 3, wherein the selection of the voxel coordinate orientation and the generation of the second voxel-based resampled image implements a slice extraction operation, wherein the second voxel-based resampled image is an image slice aligned with the selected voxel coordinate orientation.

5. The non-transitory computer-readable medium of claim 1, wherein the non voxel image elements are blob elements, point cloud elements, or spatially overlapping image elements.

6. The non-transitory computer-readable medium of claim 1, wherein the non voxel image elements are spatially overlapping image elements in which at least neighboring non voxel image elements spatially overlap in the non-voxel-based reconstructed image.

7. The non-transitory computer-readable medium of claim 1, wherein the non transitory computer-readable medium further stores image reconstruction operations executable by an image reconstruction device different from the workstation to: (i) perform an image reconstruction optimizing the non voxel image elements to generate the non-voxel-based reconstructed image; and (ii) store the non-voxel-based reconstructed image at the PACS.

8. The non-transitory computer-readable medium of claim 7, wherein the non-voxel image elements are optimized for a maximum voxel resolution value of the selected non-voxel image element; and
the generating of the at least one voxel-based reconstructed image comprises generating at least one voxel-based reconstructed image with the maximum voxel resolution and at least one voxel-based reconstructed image with the voxel resolution that is coarser than the maximum resolution.

9. An imaging system, comprising:
an image acquisition device of a modality configured to acquire imaging data of a patient;
an image reconstruction device programmed to generate a non-voxel-based reconstructed image from the imaging data using non voxel-image elements selected from at least one of blob elements, point cloud elements, or spatially overlapping image elements;
a display device; and
at least one electronic processor programmed to:
retrieve the non-voxel-based reconstructed image comprising non voxel image elements from a picture and archiving communication system (PACS) database to a workstation;
at the workstation, generate at least one voxel-based resampled image of the modality from the non-voxel-based reconstructed image;
control the display device to display the at least one voxel-based resampled image on the display device; and
generate, in real-time, at least two different voxel-based resampled images from the non-voxel-based reconstructed image by determining at least a maximum or minimum standard uptake value of the non-voxel image elements of the non-voxel-based reconstructed image, wherein the different voxel-based resampled images differ by at least one of different voxel sizes and different voxel coordinate orientations.

10. The imaging system of claim 9, wherein the at least one electronic processor is further programmed to:
control the display device) to display a first voxel-based resampled image of the at least two different voxel-based resampled images;
receive one or more user inputs, via a user input device of the workstation, indicative of a selection of a region of the first voxel-based resampled image; and
generate a second voxel-based resampled image of the at least two different voxel-based resampled images from the non-voxel-based reconstructed image, wherein the second voxel-based resampled image is a resampling of the selected region of the first voxel-based resampled image using a different voxel size than that of the first voxel-based resampled image.

11. The imaging system of claim 9, wherein the at least one electronic processor is further programmed to:
control on the display device to display a first voxel-based resampled image of the at least two different voxel-based resampled images;
receive one or more user inputs, via a user input device of the workstation, indicative of a selection of a voxel coordinate orientation in the displayed first voxel-based resampled image wherein the selected voxel coordinate orientation is different from a voxel coordinate orientation of a first voxel-based reconstructed image; and
generate a second voxel-based resampled image of the at least two different voxel-based resampled images from the non-voxel-based reconstructed image wherein the second voxel-based resampled image has the selected voxel coordinate orientation.

12. The imaging system of claim 11, wherein the selection of the voxel coordinate orientation and the generation of the second voxel-based resampled image implements a slice extraction operation, wherein the second voxel-based resampled image is an image slice aligned with the selected voxel coordinate orientation.

13. The imaging system of claim 9, wherein the image reconstruction device is programmed to store the non-voxel-based reconstructed image at the PACS for retrieval by the workstation.

14. An imaging system, comprising:
an image acquisition device of a modality configured to acquire imaging data of a patient;
an image reconstruction device programmed to generate a non-voxel-based reconstructed image from the imaging data using non-voxel image elements selected from at least one of blob elements, point cloud elements, or spatially overlapping image elements;
a picture and archiving communication system (PACS) database configured to store the non-voxel-based reconstructed image;
a workstation comprising a display device, a user input device, and at least one electronic processor programmed to:
retrieve the non-voxel-based reconstructed image comprising non voxel image elements from the PACS database to a workstation;
at the workstation: generate at least one voxel-based resampled image from the non-voxel-based reconstructed image, the different voxel-based resampled images differing by at least one of different voxel sizes and different voxel coordinate orientations;
control the display device to display the at least one voxel-based resampled image on the display device; and
generate, in real-time, at least two different voxel-based resampled images from the non-voxel-based reconstructed image by determining at least a maximum or minimum standard uptake value of the non-voxel image elements of the non-voxel-based reconstructed image, wherein the different voxel-based resampled images differ by at least one of different voxel sizes and different voxel coordinate orientations.

15. The imaging system of claim 14, wherein the at least one electronic processor is further programmed to:
control the display device to display a first voxel-based resampled image of the at least two different voxel-based resampled images;

receive one or more user inputs, via the user input device, indicative of a selection of a region of the first voxel-based resampled image; and generate a second voxel-based resampled image of the at least two different voxel-based resampled images from the non-voxel-based reconstructed image;

wherein the second voxel-based resampled image is a resampling of the selected region of the first voxel-based resampled image reconstructed using a different voxel size than that of the first voxel-based resampled image.

16. The imaging system of claim 14, wherein the at least one electronic processor is further programmed to:

control on the display device to display a first voxel-based resampled image of the at least two different voxel-based reconstructed images;

receive one or more user inputs, via the user input device of the workstation, indicative of a selection of a voxel coordinate orientation in the displayed first voxel-based resampled image wherein the selected voxel coordinate orientation is different from a voxel coordinate orientation of the first voxel-based resampled image; and generate a second voxel-based resampled image of the at least two different voxel-based resampled images from the non-voxel-based reconstructed image wherein the second voxel-based resampled image has the selected voxel coordinate orientation.

17. The imaging system of claim 16, wherein the selection of the voxel coordinate orientation and the generation of the second voxel-based resampled image implements a slice extraction operation, wherein the second voxel-based resampled image is an image slice aligned with the selected voxel coordinate orientation.

* * * * *